United States Patent
Huang et al.

(10) Patent No.: US 10,866,238 B2
(45) Date of Patent: Dec. 15, 2020

(54) ALPHA METHYLACYL A COENZYME RACEMASE DETECTION

(71) Applicant: Wisconsin Alumni Research Foundation, Madison, WI (US)

(72) Inventors: Wei Huang, Madison, WI (US); David F. Jarrard, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 268 days.

(21) Appl. No.: 15/383,437

(22) Filed: Dec. 19, 2016

(65) Prior Publication Data
US 2017/0097351 A1 Apr. 6, 2017

Related U.S. Application Data

(62) Division of application No. 11/759,098, filed on Jun. 6, 2007, now abandoned.

(60) Provisional application No. 60/804,025, filed on Jun. 6, 2006.

(51) Int. Cl.
*G01N 33/573* (2006.01)
*G01N 33/574* (2006.01)

(52) U.S. Cl.
CPC ..... *G01N 33/573* (2013.01); *G01N 33/57434* (2013.01); *G01N 2333/99* (2013.01)

(58) Field of Classification Search
CPC ........... G01N 33/573; G01N 33/57434; G01N 2333/99
See application file for complete search history.

(56) References Cited

U.S. PATENT DOCUMENTS

| | | | |
|---|---|---|---|
| 6,187,551 B1 | 2/2001 | Holmes | |
| 7,332,290 B2 | 2/2008 | Rubin et al. | |
| 2003/0108963 A1 | 6/2003 | Schlegel | |
| 2006/0084133 A1 | 6/2006 | Yuan | |

OTHER PUBLICATIONS

Chen, Z. M. et al, "Differential expression of alpha-methyl coenzyme A racemase in adenocarcinomas of the small and large intestines," Am J Surg Pathol, 2005, 29(7):890-896.
Cormier, L. et al, "Impact of prostate cancer screening on health-related quality of like in at-risk families," Urology, 2002, 59(6):901-906.
Daja, M. M. et al, "Beta-human chorionic gonadotropin in semen: a marker for early detection of prostate cancer?." Molecular Urol, 2000, 4(4):421-427.
Goessl, C., et al. "Fluorescent methylation-specific polymerase chain reaction for DNA-based detection of prostate cancer in bodily fluids," Cancer Res, 2000, 60:5941-5945.
Gologan, A. et al, "Age-associated changes in alpha-methylacyl-CoA coenxyme racemase (AMACR) expression in nonneoplastic prostatic tissues," Am J Surg Pathol, 2005, 29(11):1435-1441.
Jiang, Z. et al, "Expression of alpha-methyl-CoA coenxyme racemase (P504s) in various malignant neoplasms and normal tissues:a study of 761 cases," Hum Pathol, 2003, 34(8):792-796.
Kourilov, V. and Steinitz M., "Magnetic-bead enzyme-linked immunosorbent assay verifies adsorption of ligand and epitope accessibility," Anal Biochem, 2002, 311:166-170.
Nikkola, J. et al. "High serum levels of matrix metalloproteinase-9 and matrix metalloproteinase-1 are associated with rapid progression in patients with metastatic melanoma," Clin Cancer Res, 2005, 11(14):5158-5166.
Polascik, T.J. "Prostate specific antigen: a decade of discovery—what we have learned and where we are going," J Urol, 1999, 162(2):293-306.
Rogers, C. G. et al. "Prostate cancer detection on urinalysis for alpha methylacyl coenzyme A racemase protien," J Urol, 2004, 172:1501-1503.
Schroder, F. H. et al. "Prostate-specific antigen-based early detection of prostate cancer—validation of screening without rectal examination," Urol, 2001, 57(1):83-90.
Sreekumar, A, et al. "Humoral immune response to alpha-methyl-CoA racemase and prostate cancer," J Natl Cancer Inst, 2004, 96(11):834-843.
Tretiakova, M. S. et al, "Expression of alpha-methyl-CoA racemase in papillary renal cancer carcinoma," Am J Surg Pathol, 2004, 28(1):69-76.
Witkiewicz, A. K., et al, "Alpha-methyl-CoA racemase protein expression is associated with the degree of differentiation in breast cancer using quantitative image analysis," Cancer Epidemiol Biomarks Prev, 2005, 14 (6):1418-1423.
Zielie, P. J. et al. "A novel diagnostic test for prosate cancer emerges from the determination of alpha-methylacyl-coenzyme A racemase in prostatic secretions," J Urol, 2004, 172(3):1130-1133.
Roberts, et al., Seminal fluid: a useful source of prostate cancer biomarkers? Biomark. Med. 2015; 9(2): 77-80.
Kambiz, et al., Exploring the Human Seminal Plasma Proteome: An Unexplored Gold Mine of Biomarker for Male Infertility and Male Reproduction Disorder. J Reprod Infertil. 2015; 16(2): 61-71.
DeMarzo, et al., Pathological and molecular aspects of prostate cancer. The Lancet. 2003; 361: 955-964.

*Primary Examiner* — Teresa E Knight
(74) *Attorney, Agent, or Firm* — Quarles & Brady LLP

(57) ABSTRACT

A method of detecting the presence or absence of alpha methylacyl A coenzyme racemase (AMACR) is provided. In one embodiment of the method, a fluid including a secretion chosen from at least one of a prostate secretion or a secretion from an accessory glad or a cellular component of the fluid is obtained from a subject. The fluid is contacted with a reagent for detecting AMACR under conditions such that the reagent detects AMACR in the semen. The level of AMACR is determined such as by comparing it to a standard curve. The fluid can be semen or a prostate secretion or another fluid. A kit that can be used with the method is also provided.

6 Claims, 2 Drawing Sheets

ALPHA METHYLACYL A COENZYME RACEMASE DETECTION

CROSS-REFERENCE TO RELATED APPLICATIONS

This application is a divisional application of U.S. patent application Ser. No. 11/759,098, filed Jun. 6, 2007, which claims priority under 35 U.S.C. § 119(e) to U.S. Provisional Patent Application No. 60/804,025, filed Jun. 6, 2006, each of which is incorporated by reference herein.

BIBLIOGRAPHY

Complete bibliographic citations of the references referred to herein by bracketed numerals can be found in the Bibliography section, immediately preceding the claims. The references listed in the bibliography are incorporated by reference into the application in their entireties.

FIELD OF THE INVENTION

The invention relates to methods of and kits for diagnosing cancer and precancerous conditions and for determining prognosis in a cancer patient, and more particularly to methods of and kits for diagnosing prostate cancer and precancerous prostate condition and for determining prognosis in a prostate cancer patient.

DESCRIPTION OF THE RELATED ART

Prostate cancer is the most common cancer for men in the U.S. In 2005, over 232,000 men will be diagnosed with prostate cancer, and over 30,000 men will die from it. One new case occurs every 2.5 minutes and a man dies from prostate cancer every 17 minutes. After lung cancer, prostate cancer is the leading cause of cancer-related deaths among men in the U.S.

Early prostate cancer usually has no symptoms and is most commonly detected through prostate cancer screening tests such as the prostate specific antigen (PSA) blood test and digital rectal exam (DRE). Both tests have their limitations, PSA is elevated in both benign and malignant prostate diseases and has only 30% specificity, so it is a non-specific test. A digital rectal examination allows a doctor to feel only the back wall of the prostate gland, any abnormalities located in the middle or front part of the gland cannot be felt. Thus, the DRE and PSA tests cannot diagnose prostate cancer; they merely indicate that further testing is needed.

Biopsy remains the gold standard in the diagnosis of prostate cancer. A prostate needle biopsy is a surgical procedure in which a small sample of tissue is removed from the prostate gland and examined under the microscope by a pathologist to make a diagnosis. While biopsies are the most accurate means of detecting the presence of cancer in the prostate, it is possible to miss a significant cancer during a biopsy—or receive a false-negative result. Prostate cancer does not typically grow as one single tumor or grouping of cancer cells. Rather, prostate cancer is usually comprised of many different small tumors or cancer cell groupings in different areas of the prostate. For this reason, the exact location of these various small tumors can be difficult to pinpoint with the biopsy needles. Moreover, it is a costly and painful procedure with complications, such as bleeding, infection and urinary retention. Each year many men with persistently elevated PSA are subject to prostate biopsy. But only 30% are diagnosed with cancer on first biopsy. [2] The rest of them may have to go through repeat biopsies without finding any evidence of malignancy, but still live with anxiety. [1]

Alpha methylacyl A coenzyme racemase (AMACR) is a peroxisomal and mitochondrial enzyme involved in the β-oxidation of branched fatty acids. The gene encoding AMACR is over-expressed in prostate cancer. Currently, AMACR immunohistochemical staining has become a common practice in morphologically diagnosing small, morphologically ambiguous prostate cancer in biopsy specimen. AMACR is also known as P504S. [3-6] Although serum AMACR has been reported undetectable, studies have shown that AMACR protein and mRNA can be detected from urine cellular component post prostate biopsy or massage manipulation. [7, 8] However, this detection requires collecting exfoliated cancer cells by prostate biopsy or massage manipulation. A humoral immune response against AMACR in prostate cancer patients has also been reported recently. [9]

The major component of the semen ejaculate volume (average 5 mL) is made up of secretions from the accessory glands. Between 0.5 and 1 ml originates from the prostate. Studies have shown that some other putative prostate cancer biomarkers (beta HCG and GSTP1) have been detected in semen ejaculate. [10, 11]

In view of the foregoing, it would be desirable to provide a specific test that can identify patients who have prostate cancer or precancerous disorder and that is superior to the current non-specific screening test, i.e., the PSA test. There is also a need for a more accurate, non-invasive method of diagnosing prostate cancer.

SUMMARY OF THE INVENTION

The invention is intended to solve at least some of the problems noted above. A method of detecting the presence or absence of alpha methylacyl A coenzyme racemase (AMACR) is provided.

In one embodiment of the method, a fluid including a secretion chosen from at least one of a prostate secretion or a secretion from an accessory glad or a cellular component of the fluid is obtained from a subject. The fluid is contacted with a reagent for detecting AMACR under conditions such that the reagent detects AMACR in the semen. The level of AMACR is determined such as by comparing it to a standard curve.

The fluid can be semen or a prostate secretion or another fluid.

The presence of AMACR at a level above a minimum age-appropriate threshold level can be used as an indication of a diagnosis of prostate cancer or a precancerous prostate condition in the subject.

In one embodiment of the method, the method is for diagnosing prostate cancer or a precancerous prostate condition in a subject. In the method, a sample including a secretion chosen from at least one of a prostate secretion or a secretion from an accessory gland or a cellular component of the fluid from the subject is provided. A level of alpha methylacyl A coenzyme racemase (AMACR) in the sample is detected. The level of AMACR present in the sample is used to determine whether the subject has prostate cancer or a precancerous prostate condition.

The reagent used in the methods can be an antibody. The antibody is capable of forming a complex with the AMACR. The amount of complex formed can be determined and used as a measure of the presence or amount of AMACR in the semen. The amount of complex determined can be used as an indication of a diagnosis of prostate cancer, a precancerous condition, or a prognosis of prostate cancer in the subject.

In one embodiment, the antibody includes a label, such as an enzyme, a radioactive label, a fluorescent label, a fluorescence emitting metal, a chemiluminescent label, a chromophoric label, a bioluminescent label, or another label known in the art.

Also provided is a method for diagnosing prostate cancer or a precancerous prostate condition in a subject. In one embodiment of the method, a semen sample from the subject is provided. A level of AMACR in the sample is detected. The level of AMACR present in the sample is used to determine whether the subject has prostate cancer or a precancerous prostate condition.

The level of AMACR can be detected by exposing the sample to a first antibody specific to AMACR and detecting binding of the antibody to AMACR. A second antibody specific to AMACR can be provided, as can a third antibody. At least one the second and third antibody can include a label, such as an enzyme, a radioactive label, a fluorescent label, a fluorescence emitting metal, a chemiluminescent label, a chromophoric label, a bioluminescent label, or another label known in the art. The subject can be a human subject.

Kits are also provided. In one embodiment, the kit includes a positive control that reacts with a reagent for detecting AMACR and a negative control that does not react with the reagent.

The kit can also include a reagent capable of detecting AMACR, such as a first antibody that binds to AMACR. A second antibody that detects AMACR can also be included, as well as a third antibody that binds to the second antibody. At least one of the second antibody and the third antibody can include a label.

BRIEF DESCRIPTION OF THE DRAWINGS

Preferred exemplary embodiments of the invention are illustrated in the accompanying drawings, in which like reference numerals represent like parts throughout and in which.

Figure 1:
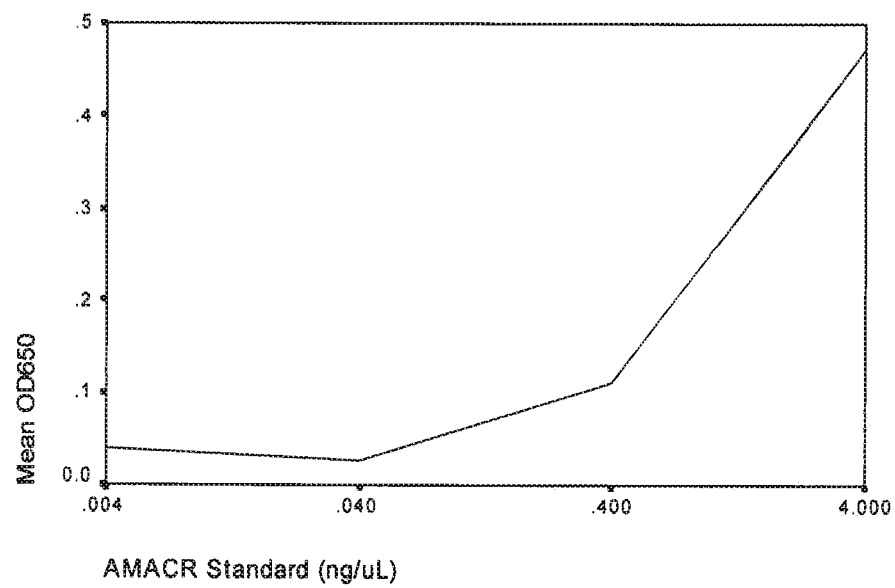
FIG. 1 is a graph showing the results of ELISA detection of serially diluted, control AMACR samples.

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

1. Introduction

Provided are methods and kits for detecting biomarkers of prostate cancer and precancerous prostate condition, such as alpha methylacyl A coenzyme racemase (AMACR) or CXCL14, in a fluid containing secretions or a molecular marker in a cellular component of fluid containing secretions. For instance, AMACR can be detected in semen or prostate secretion. In one embodiment, the methods and/or kits are used on semen ejaculate to diagnose prostate cancer or a precancerous prostate condition. AMACR and the other biomarkers can be detected using an immunoassay. One embodiment of the immunoassay is an ELISA, which can include a primary antibody that recognizes the biomarker, such as AMACR. The antibody-antigen complex is then detected, such as with one or more additional antibody, as in a sandwich ELISA assay. The inventors have demonstrated the presence of AMACR in prostate secretion, the major component of semen ejaculate of prostate cancer patients, and in semen. The major component of the semen ejaculate volume (average 5 mL) is made up of secretions from the accessory glands. Between 0.5 and 1 ml of semen ejaculate originates from the prostate. Proteins secreted by the prostate gland may be detected without an added step of disrupting cellular components thereby making the proteins accessible to detection.

AMACR has been reported in other tissues including breast tissue [12] and lung [13]. As the protein is detected in these tissues, the protein may be detectable in secretions from these tissues as well.

2. Immunoassays

The present invention relates to antigen(s) or antibody(ies) capable of binding to an analyte to identify and/or quantify substances. The antibody can be a polyclonal antibody, a single chain antibody, an Fab fragment, a monoclonal antibody (MAB), a polyclonal antibody, and a recombinant antibody. The analyte can be an antigen, an antibody, or it can be another analyte. In general, immunoassays include providing a sample having an epitope bindable by an antibody against the epitope. The sample is incubated under conditions that allow for the formation of an antibody-antigen complex. The presence or absence of the antibody-antigen complex is then determined.

Types of immunoassays include competitive and non-competitive assay systems using techniques, including, but not limited to, radioimmunoassay, ELISA (enzyme linked immunosorbent assay), "sandwich" immunoassay such as sandwich ELISA assay, immunoradiometric assay, gel diffusion precipitin reaction, immonodiffusion assay, precipitation reaction, agglutination assay (e.g., gel agglutination assay, hemagglutination assay), complement fixation-assay, immunofluorescence assay, protein A assay, and immunoelectrophoresis assay, and Western blot.

Immunoassays for AMACR or another biomarker will typically comprise incubating a sample including secretions, such as semen, in the presence of an antibody and detecting the antibody-antigen complex by any of a number of techniques well known in the art.

In one embodiment, an antibody to the biomarker is immobilized on a solid phase support or carrier, such as a plate. For sake of convenience only, the remaining steps will be described with respect to a plate. However, it should be understood that other supports or carriers can be used. The plate is washed to remove unbound antibody. The plate can be blocked with, e.g., BSA PBS, to prevent non-specific binding. The plate is washed to remove excess BSA PBS.

The sample is brought in contact with the antibody immobilized on the plate to allow for formation of biomarker:antibody complex. The plate may then be washed with suitable buffers followed by treatment with the antibody. The plate may then be washed with the buffer a second time to remove unbound sample.

The biomarker:antibody complex can be detected by any of a number of techniques well known in the art. In one embodiment, a second antibody that detects the biomarker is added. The plates are washed to remove the second antibody that is unbound. A third antibody that detects the second antibody is then added. The plates are washed to remove the third antibody that is unbound.

The amount of bound biomarker on the solid support may then be detected by conventional means. For example, the third antibody can be linked to a label, including, but not limited to a radioisotope, an enzyme that catalyses a reaction, and a fluorescent compound.

In another embodiment, a second antibody that detects the biomarker or the biomarker:antibody complex is added and linked to a label is added such that the second antibody can be detected.

When an antibody is linked to an enzyme, the enzyme will react with an appropriate substrate, preferably a chromogenic substrate, in such a manner as to produce a chemical moiety that can be detected, for example, by spectrophotometric, fluorimetric, or by visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

For colorimetric detection of antibody that is covalently bound to an enzyme, horseradish peroxidase-conjugated anti-mouse antibody used in conjunction with the substrate 3,3',5,5'-tetramethylbenzidine (TMB) is preferred. Other peroxidase substrates, such as o-phenylenediamine dihydrochloride (OPD) and anti-mouse alkaline phosphatase conjugates can also be used.

Detection may also be accomplished using any of a variety of other ways. For example, by radioactively labeling the antibody or fragment, it is possible to detect the antigen that the antibody was designed for through the use of a radioimmunoassay (RIA). The radioactive isotope can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

In addition, it is possible to label the antibody with a chromophoric label, such as ultraviolet-absorbing or visible light-absorbing labels.

Likewise, a bioluminescent compound may be used to label the antibody of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In a non-limiting, illustrative embodiment, an ELISA assay is employed. In general, an antibody against the protein or other analyte of interest is immobilized on an inert solid, e.g., polystyrene. For sake of simplicity, the remaining description of an ELISA assay will be limited to detection of a protein. As was discussed above, other analytes can be detected with an ELISA assay. A sample to be assayed for the protein of interest is applied to the surface containing immobilized antibody. Protein binds the antibody, forming a complex. This complex is then contacted by a second antibody that binds the same protein. The second antibody can be covalently bound to a label, such as an enzyme. Alternatively, a third antibody can be used to detect the second antibody. In this instance, the second antibody can be covalently bound to a label, such as an enzyme. After washing away any unbound second antibody (and unbound third antibody, where used), the label is visualized. For example, where the antibody is covalently bound to an enzyme, the enzyme in the immobilized complex is assayed, providing a measurement of the amount of protein in the sample. The ELISA procedure can be reversed, i.e., the antigen is immobilized on an inert support (e.g., 96-well microplate) and samples are probed for the presence of antibody to the immobilized antigen.

3. Samples

AMACR and other biomarkers can be detected and quantified in samples that are fluids that include secretions and in secretions themselves. These fluids include, but not limited to, breast milk, lung sputum, and semen. These samples may be of human origin or they may be taken from animals other than humans, for example, avian species, but preferably mammals. The disclosed methods and kits (described below) can be used on samples of breast milk for diagnosing breast cancer and precancerous breast condition, samples including, but not limited to, lung sputum for diagnosing lung cancer and precancerous lung condition, samples of semen for diagnosing prostate cancer and precancerous prostate condition, and samples of prostrate secretion for diagnosing prostate cancer and precancerous prostate condition. The methods and kits could be used to detect solid tumors.

The methods and kits can also be used to determine a patient's prognosis. For this, the level of AMACR or other biomarker is used to determine a patient's prognosis. For example, a lower level of the biomarker would indicate an improvement in the cancerous condition.

4. Kits

An additional aspect of the present invention relates to kits for the detection or measurement of AMACR or another biomarker. Where the kit is the detection or measurement of AMACR, the kit includes a positive control that reacts with a reagent for detecting AMACR and a negative control that does not react with the reagent. In one embodiment, the positive control is AMACR. The AMACR can be provided in multiple containers containing predetermined amounts of AMACR or in a single container.

The kit can also include a reagent capable of detecting AMACR. In one embodiment, the kit the reagent comprises a first antibody that binds to AMACR.

The kit can also include a second antibody that detects AMACR. A third antibody that binds to the second antibody can also be included. At least one of the second antibody and the third antibody can further comprises a label. The label can be selected from the group consisting of an enzyme, a radioactive label, a fluorescent label, a fluorescence emitting metal, a chemiluminescent label, a chromophoric label, and a bioluminescent label

EXAMPLES

The following Examples are provided for illustrative purposes only. The Examples are included herein solely to aid in a more complete understanding of the presently described invention. The Examples do not limit the scope of the invention described or claimed herein in any fashion.

Example 1

ELISA Detection of AMACR in Prostate Secretion:
Method:

The following method was used for a two antibody sandwich test. A plate (MTX Lab Systems, Inc., Vienna, Va.) was coated with rabbit monoclonal anti-AMACR (Zeta Corporation, Sierra Madre, Calif.) 10 ug/mL 50 ul/well and incubated at 4° C. overnight. The plate was washed with PBS two times. The plate was blocked with 3% BSA PBS at room temperature and incubated for 2 hrs. The plate was washed with PBS two times.

Specimen was added to the plate at room temperature and incubated for 2 hrs. Prostate secretion samples obtained intraoperatively from patients known to have prostate cancer and semen ejaculate from a normal control were diluted as indicated in Tables 2-3 and added to wells at 50 ul/well. Control wells containing AMACR (US Biological, Swampscott, Mass.) were included. AMACR was denatured at 50° C. for 5 minutes before it was added to each well. The denatured AMACR was added to control wells at 50 ul/well in serial dilutions: 4 ng/uL, 0.4 ng/uL, 0.04 ng/uL and 0.004 ng/uL. The plate was washed with PBS three times. A first antibody (mouse polyclonal anti-AMACR (Abnova, 1:500) was added and incubated at room temperature for 2 hrs. The plate was washed with PBS three times. A second antibody (goat anti mouse IgG (Abeam 1:2500)) was added and incubated at room temperature for 2 hrs. The plate was washed with PBS four times. 3,3',5,5'-tetramethylbenzidine (TMB) substrate, a colorimetric substrate, was added to the wells. The plate was read at 650 nm wavelength on a standard ELISA reader.
Results:

Results of the ELISA detection of the serially diluted, control AMACR samples were as shown in Table 1 below and as shown in FIG. 1.

TABLE 1

Control AMACR Samples

| AMACR | 4 ng/uL | 0.4 ng/uL | 0.04 ng/uL | 0.004/uL |
|---|---|---|---|---|
| OD650 | 0.472 | 0.109 | 0.026 | 0.038 |

The results of the two antibody sandwich test on the serially diluted AMACR samples show a sensitivity of 0.040 ng/ul and a linear response range of 0.040 to 4.0 ng/ml.

Figure 2:
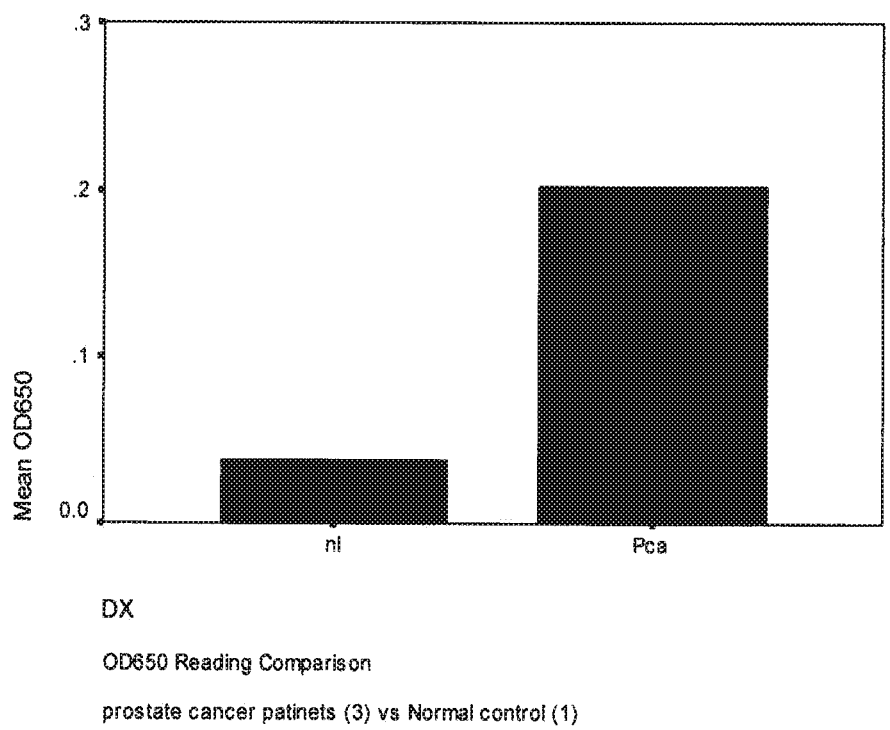
FIG. 2 is a graph showing the average results of a normal control (nl) and prostate cancer patient's (Pca).

Patient and control results are shown below in Tables 2 and 3 Patient and control (normal) samples were diluted as shown in Tables 2 and 3. An extract from sonicated prostate cancer tissue (from one paraffin section, the exact quantity unknown) was also used (see column PC in Table 2). Results from the three patients were averaged. The averaged results are shown below. Two readings were done on a single, normal control and Patients 2 and 3. The patient results were pooled and averaged. The control results were averaged. The averaged results are shown in FIG. 2.

TABLE 2

Patient and Control Samples

| Sample | PC | Patient 1 (1:6) | Patient 2 (1:2) | Patient 3 (1:6) | Normal control (1:2) |
|---|---|---|---|---|---|
| OD650 | 0.036 | 0.033 | 0.115 | 0.016 | 0.006 |

TABLE 3

Patient and Control Samples

| Sample | Patient 2 (1:4) | Patient 3 (1:2) | Normal control (1:2) |
|---|---|---|---|
| OD650 | 0.040 | 0.101 | 0.038 |

The pooled, averaged patient results showed a significant increase in the mean OD650 reading of AMACR when compared to the averaged control results, indicating that AMACR is a useful biomarker for detecting prostate cancer in semen samples.

Example 2

Figure 3:
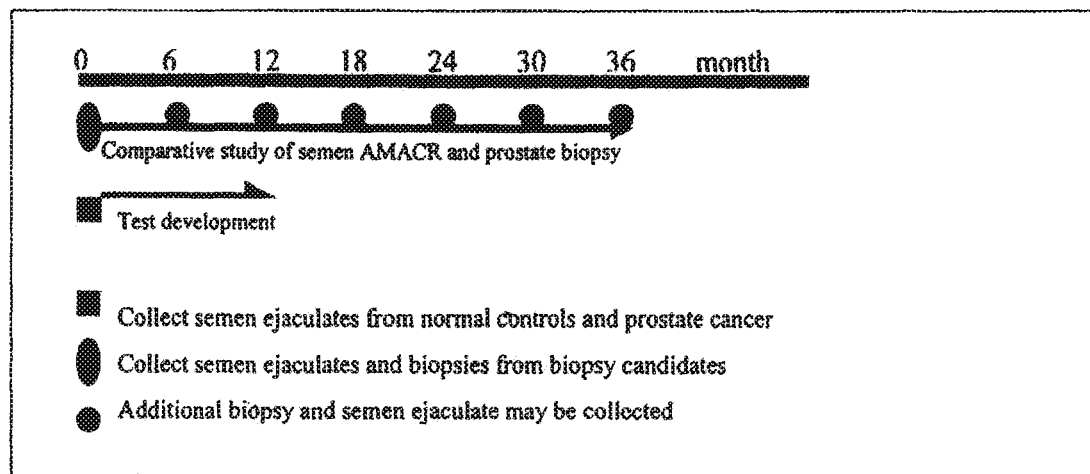
FIG. 3 is a timeline showing events related to a study described in Example 2.
Figure 4:
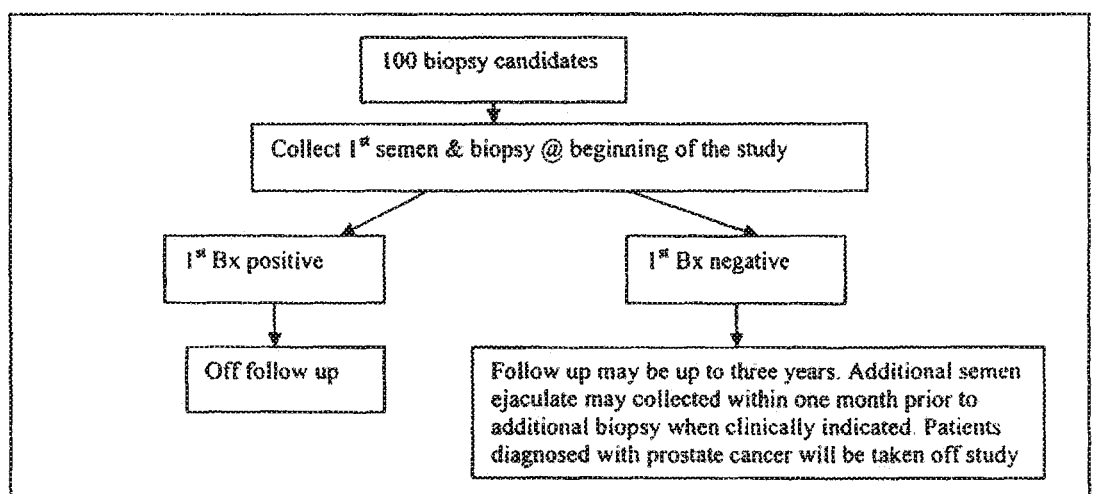
FIG. 4 is a flowchart showing handling of samples described in the study of Example 2.

Overall Summary:

The purpose of this study is to develop a novel, non-invasive and specific test for screening and diagnosis of prostate cancer. Three groups of people will be studied: 30 normal healthy young men, 30 prostate cancer patients prior to surgery and 100 prostate biopsy candidates. Semen ejaculate will be collected from all subjects. AMACR in semen ejaculate will be quantified by enzyme linked immunosorbent assay (ELISA). We expect to establish the assay and to define positive threshold of the test by studying semen AMACR in prostate cancer patients and normal controls, and to conduct comparative study of semen AMACR test and prostate biopsy in 100 biopsy candidates and follow up these patients for up to three years to study the predictive value of semen AMACR test, as is further detailed in FIGS. 3 and 4.
Hypothesis:

AMACR is present in the semen ejaculate of prostate cancer patients, can be utilized to detect to identify patients with prostate cancer.

Specific Aims:

1) To determine AMACR positive threshold by studying 30 normal controls and 30 patients with diagnosed prostate cancer. 2) To evaluate AMACR test statistically in 100 men undergoing prostate biopsy.

Design:

Subjects:

1. 30 healthy young men (<30 y), as normal controls
2. 100 men who are candidates for prostate biopsy
3. 30 patients with diagnosed prostate cancer, as positive control Eligibility for Subjects in Group 1:

1. Must be an adult man, 18-30 years old.
2. Must have no known history of cancer or malignancy.
3. Subjects must give written informed consent for the study protocol.

Eligibility for Subjects in Group 2:

1. Must be an adult man, 18 years or older
2. Subjects must be a candidate for a prostate biopsy and be considered at high risk to develop prostate cancer
3. Subjects must give written informed consent for the study protocol.

Eligibility for Subjects in Group 3:

1. Must be an adult man, 18 years or older.
2. Must have histologically proven cancer of the prostate gland with prostatectomy scheduled no more than 1 month from time of collection.
3. Subjects must give written informed consent for the study protocol.

Methods:

Enzyme-linked immunosorbent assay (sandwich ELISA) will be used to detect and quantitate AMACR protein in semen ejaculate.

Expected Outcomes:

AMACR will be detected and quantitated in semen ejaculates by ELISA. AMACR ELISA will be a non-invasive, specific test to be used for screening and diagnosis of prostate cancer. It may replace current serum PSA test eventually.

Approaches:

Specimen and Data Collection:

All participants will be registered with the GU Disease Oriented Working Group and will be assigned with a study number. Subject information will be stored in University of Wisconsin Comprehensive Cancer Center data entry system (Oncore).

Semen will be collected from all participants at the clinic. Subjects will be instructed to collect the semen in a study-supplied container pre-labeled with the subject's study ID number. The specimen will need to be kept cold at 4 degrees Celsius. All specimens will be handled using Universal Precautions.

Semen ejaculates will be collected only once from subjects in Group 1 and Group 3. Subjects in Group 3 will be requested to provide the sample within one month prior to prostatectomy.

Subjects in Group 2 will be asked to provide semen ejaculate within one month prior to their prostate biopsy at the beginning of their study participation. Additional semen ejaculate may be collected prior to additional prostate biopsies, only when clinically indicated, in the three year follow up period.

Method:

Seminal fluid will be separated from semen ejaculate to test for AMACR or other potential biomarkers (e.g., CXCL14). The cellular components of semen ejaculates will be saved and stored in freezer at −80° C. for future molecular analysis.

ELISA:

Standard (purified AMACR protein) and seminal fluid samples are incubated in a microwell plate precoated with rabbit anti-AMACR monoclonal antibodies (Zeta-Corp, Sierra Madre, Calif.). Any AMACR present in the samples is bound to the wells, and the excess was removed by extensive washing. AMACR is then detected by mouse anti-AMACR polyclonal antibody (Abnova, Taipei, Taiwan). A secondary peroxidase labeled anti-mouse Ig polyclonal antibodies (Abcam, Cambridge, Mass.), and the amount of peroxidase is determined by addition of TMB substrate. Reactions are stopped by adding acid solution and the absorbance was read at 650 nm in a microtiter plate spectrophotometer. AMACR concentrations are determined from the corresponding standard curves run for each plate separately.

Anticipated Result:

A distinct difference in AMACR levels in semen ejaculates will be present between cancer patients and normal controls. AMACR will be significantly elevated in all patients with positive biopsy. AMACR test will predict prostate cancer. Some patients may have AMACR elevation but negative biopsy. The discordance would be primarily due to the limitation of biopsy, or due to a precancerous condition—high grade prostate intraepithelial neoplasia (HGPIN), which is also associated with AMACR elevation.

Statistical Justification:

The sample sizes chosen for the three groups are sufficient to provide accurate estimates of the specificity and sensitivity of our proposed procedure. Specifically, with a proposed sample size of 30 subjects in the normal control group (Group 1) and a sample size of 30 subjects in the positive control group (Group 3), the standard error of the estimated specificity/sensitivity will be less than 10%. Moreover, the 95% confidence intervals for the sensitivity and specificity will be no wider than 33%. The specificity of PSA testing is 60% to 70% while the sensitivity is between 70%-80%. [2, 14] For the proposed AMACR testing, a specificity of at most 60% and a sensitivity of at most 70% would be considered as clinically irrelevant. On the other hand, a specificity of at least 80% or a sensitivity of at least 90% would warrant further investigation. Therefore, we will test the null hypothesis that the specificity of the proposed AMACR testing is at most 60% versus the alternative hypothesis that the specificity is greater than 60%. Analogously, we will test the null hypothesis that the sensitivity of the proposed AMACR testing is at most 70% versus the alternative hypothesis that the specificity is greater than 70%. Assuming a sample size of 30 normal control subjects (Group 1), a specificity of at least 80% will be detected with 78% power at a (one)-sided significance level of 0.05 (=0.10/2—a Bonferroni adjustment for multiple (specificity and sensitivity) comparisons). A specificity of 85% will be detected with 93% power. Assuming a sample size of 30 subjects diagnosed with prostate cancer (Group 3), a sensitivity of at least 90% will be detected with 83% power at a (one)-sided significance level of 0.05. A sensitivity of 95% will be detected with 98% power. A target sample size of 100 biopsy candidates (Group 2) is proposed. It is anticipated that between 25-30% will have a positive biopsy. [2, 14] Hence, the standard error for the estimated specificity in this group will be at most 6% while the standard error for the estimated sensitivity will be at most 9%. Furthermore, the 95% confidence interval for the specificity in this group will be no wider than 22% and the 95% confidence interval for the sensitivity will be no wider than 33%.

Results Obtained:

We collected semen ejaculate specimens from 30 young (<30 years) volunteers from Group 1 and 7 prostate cancer patients from Group 3. AMACR levels were tested in these specimens following the method described in Example 1. Results are shown in Table 4 below.

TABLE 4

Colorimetric Sandwich ELISA Results From Ejaculates

| Subject | Dx | AMACR (ng/mL) |
|---|---|---|
| #1 | nl | n |
| #2 | nl | n |
| #3 | nl | n |
| #4 | nl | n |
| #5 | nl | n |
| #6 | nl | 200 |
| #7 | nl | 630 |
| #8 | nl | n |
| #9 | nl | 160 |
| #10 | nl | n |
| #11 | nl | n |
| #12 | nl | 156 |
| #13 | nl | n |
| #14 | nl | 937 |
| #15 | nl | 80 |
| #16 | nl | n |
| #17 | nl | n |
| #18 | nl | 40 |
| #19 | nl | 42 |
| #20 | nl | n |
| #21 | nl | n |
| #22 | nl | 78 |
| #23 | nl | 756 |
| #24 | nl | n |
| #25 | nl | n |
| #26 | nl | n |
| #27 | nl | n |
| #28 | nl | 156 |
| #29 | nl | n |
| #30 | nl | n |
| #31 | Pca | n |
| #33 | Pca | 60 |
| #34 | Pca | n |
| #36 | Pca | 40 |
| #35 | Pca | n |
| #37 | Pca | 320 |
| #38 | Pca | n | nl = young normal control  Pca = prostate cancer  n = undetectable

AMACR concentrations were determined from the corresponding standard curves run for each plate separately. The sensitivity of our colorimetric sandwich ELISA assay was 40-5000 ng/mL.

AMACR was detected in the specimens from 10 of the 30 young controls (Group 1) and 3 of 7 cancer patients with low volume cancer (1-10%) by biopsy (Table 4). A recent study found that baseline AMACR expression level in benign prostate glands is reversely correlated with age. AMACR expression level is very low or undetectable in men over 45 years old [15]. To confirm the existence of this correlation, we are recruiting age-comparable normal volunteers. Once these data from this control group are available, these data can be used to establish an age-appropriate threshold for AMACR.

In addition, some of the samples from prostate cancer patients in Table 4 had an undetectable level of AMACR. It is therefore possible that the samples were of poor quality. To check for this possibility, we plan to measure the concentration of a ubiquitous semen protein, PSA, in sera of the ejaculate samples as specimen quality control. PSA concentrations will be measured using an electrochemiluminescence immunoassay such as Elesys from Roche Diagnostics, North America.

Example 3

Realizing that colorimetric sandwich ELISA has limited sensitivity, we also developed a more sensitive chemiluminescence sandwich ELISA, which is the same as the colorimetric assay described in Example 1 except that a chemiluminescence peroxidase substrate (Sigma-Aldrich, St. Louis, MICROORGANISM, Cat. No. CPS1-60) was used instead of a colorimetric substrate. The chemiluminescent substrate was used per the manufacturer's instructions. Briefly, 50 ul of substrate diluted 1:2 with the solution provided in the kit, was added to each well. The reaction of chemiluminescent assay is recorded by a chemiluminescence microplate reader (TR 711 Microtiter Luminometer, PE Applied Biosystems, Foster City, Calif.) The sensitivity of chemiluminescent assay was 7.8-500 ng/mL.

We collected 13 semen ejaculates from prostate cancer patients prior to prostatectomy and ran the chemiluminescence sandwich ELISA assay on them. Results are shown in Table 5 below. AMACR was detected in 9 of 12 patients with prostate cancer. AMACR was not detected in three patients (#31, #34 & #40). These results were consistent with the biopsy results: #40 was found with no residual tumor in the prostate after prostatectomy. #31 and #34 were found with very low cancer volume on biopsy, and were on a watchful waiting list; hence, prostatectomy was not performed.

TABLE 5

Chemiluminescent Sandwich ELISA Results from Ejaculates

| Subject | Diagnosis | Tumor volume | Gleason Score | AMACR (ng/mL) |
|---|---|---|---|---|
| #31 | Pca | 1% (B) | 3 + 3 = 6 | N |
| #33 | Pca | 20% | 4 + 3 = 7 | 125 |
| #34 | Pca | 1% (B) | 3 + 3 = 6 | N |
| #36 | Pca | 20% | 4 + 3 = 6 | 40 |
| #35 | Pca | 5% | 3 + 4 = 7 | 120 |
| #37 | Pca | 30% | 4 + 5 = 9 | N |
| #38 | Pca | 30% | 3 + 4 = 7 | 325 |
| #40 | NT | 0 | NA | N |
| #41 | Pca | 20% | 3 + 4 = 7 | 500 |
| #42 | Pca | 20% | 3 + 4 = 7 | 120 |
| #43 | Pca | 1% | 3 + 3 = 6 | 250 |
| #44 | Pca | 5-10% | 3 + 4 = 7 | 90 |
| #45 | Pca | 25% | 3 + 4 = 7 | 200 |

Pca = prostate cancer
N = negative
B = biopsy
NT = no residual tumor
Tumor volume is estimated on prostatomy specimen, if not specified.
Gleason Score (GS) is commonly used to grade prostate cancer:
GS 2-5 = well differentiated;
GS 6-7 = moderately differentiated;
GS 8-10 = poorly differentiated It is understood that the various preferred embodiments are shown and described above to illustrate different possible features of the invention and the varying ways in which these features may be combined. Apart from combining the different features of the above embodiments in varying ways, other modifications are also considered to be within the scope of the invention.

The invention is not intended to be limited to the preferred embodiments described above, but rather is intended to be limited only by the claims set out below. Thus, the invention encompasses all alternate embodiments that fall literally or equivalently within the scope of these claims.

BIBLIOGRAPHY

1. Cormier, L., et al., Impact of prostate cancer screening on health-related quality of life in at-risk families. Urology, 2002. 59(6): p. 901-6.
2. Schroder, F. H., et al., Prostate-specific antigen-based early detection of prostatecancer-validation of screening without rectal examination. Urology, 2001. 57(1): p. 83-90.
3. Witkiewicz, A. K., et al., Alpha methylacyl A coenzyme racemase protein expression is associated with the degree of differentiation in breast cancer using quantitative image analysis. Cancer Epidemiol Biomarkers Prev, 2005. 14(6): p. 1418-23.
4. Tretiakova, M. S., et al., Expression of alpha methylacyl A coenzyme racemase in papillary renal cell carcinoma. Am J Surg Pathol, 2004. 28(1): p. 69-76.
5. Chen. Z. M., J. H. Ritter, and H. L. Wang, Differential expression of alpha-methylacyl coenzyme A racemase in adenocarcinomas of the small and large intestines. Am J Surg Pathol, 2005. 29(7): p. 890-6.
6. Jiang. Z., et al., Expression of alpha methylacyl A coenzyme racemase (P504s) in various malignant neoplasms and normal tissues: astudy of 761 cases. Hum Pathol, 2003. 34(8): p. 792-6.
7. Rogers, C. G., et al., Prostate cancer detection on urinalysis for alpha methylacyl coenzyme a racemase protein. J Urol, 2004, 172(4 Pt 1): p. 1501-3.
8. Zielie, P. J., et al., A novel diagnostic test for prostate cancer emerges from the determination of alpha-methylacyl-coenzyme a racemase in prostatic secretions. J Urol, 2004. 172(3): p. 1130-3.
9. Sreekumar, A., et al., Humoral immune response to alpha methylacyl A coenzyme racemase and prostate cancer. J Natl Cancer Inst, 2004. 96(11): p. 834-43.
10. Daja, M. M., et al., Beta-human chorionic gonadotropin in semen: a marker for early detection of prostate cancer? Mol Urol, 2000. 4(4): p. 421-7.
11. Goessi, C., et al., Fluorescent methylation-specific polymerase chain reaction for DNA-based detection of prostate cancer in bodily fluids. Cancer Res, 2000. 60(21): p. 5941-5.
12. Witkiewicz, Agnieszka K., et al., α-Methylacyl-CoA Racemase Protein Expression Is Associated with the Degree of Differentiation in Breast Cancer Using Quantitative Image Analysis. Cancer Epidemiol Biomarkers Prev, 2005 14: p. 1418-1423.
13. Jiang, Z., et al., Expression of alpha-methylacyl-CoA racemase (P504s) in various malignant neoplasms and normal tissues: a study of 761 cases, Hum Pathol. 2003 August: 34(8): p. 792-6.
14. Polascik, T. J., J. E. Oesterling, and A. W. Partin, Prostate specific antigen: a decade of discovery—what we have learned and where we are going. J Urol, 1999. 162(2): p. 293-306.
15. Gologan, A., et al., Age-Associated Changes in Alpha-Methyl CoA Racemase (AMACR) Expression in Nonneoplastic Prostatic Tissues. Am J Surg Pathol, 2005. 29(11): p. 1435-41.

What is claimed is:

1. A method of detecting the presence of alpha methylacyl A coenzyme racemase (AMACR) in a semen sample, comprising:
    a) obtaining a semen sample from a subject; and
    b) contacting the semen sample with a first antibody able to form a complex with AMACR, wherein the antibody is immobilized on a solid phase support or carrier, and
    c) detecting an amount of the antibody-AMACR complex in the semen sample, wherein the amount of AMACR complex is a measure of an amount of AMACR in the semen sample; and wherein the amount of complex detected is indicative of a diagnosis of prostate cancer, a precancerous condition, or a prognosis of prostate cancer in the subject.
2. The method of claim 1, wherein a level of AMACR in the semen sample is determined by comparing it to a standard curve from purified AMACR protein.
3. The method of claim 1, wherein the presence of AMACR in the semen sample at a level above an age-appropriate minimum threshold level is indicative of a diagnosis of prostate cancer or a precancerous prostate condition in the subject.
4. The method of claim 1, wherein the antibody comprises a label selected from the group consisting of an enzyme, a radioactive label, a fluorescent label, a fluorescence emitting metal, a chemiluminescent label, a chromophoric label, and a bioluminescent label.
5. The method of claim 1, wherein the detecting the level of AMACR further comprises a second antibody specific to AMACR.
6. The method of claim 5, wherein the detecting further comprises providing a third antibody, wherein at least one of the second and third antibody includes a label.

* * * * *